United States Patent [19]

Eveleigh et al.

[11] Patent Number: 4,954,444

[45] Date of Patent: * Sep. 4, 1990

[54] ENZYME IMMOBILIZATION AND BIOAFFINITY SEPARATIONS WITH PERFLUOROCARBON POLYMER-BASED SUPPORTS

[75] Inventors: John William d. Eveleigh, Hockessin; Robert K. Kobos, Wilmington, both of Del.

[73] Assignee: E. I. Du Pont de Nemours and Company, Wilmington, Del.

[ * ] Notice: The portion of the term of this patent subsequent to Dec. 5, 2006 has been disclaimed.

[21] Appl. No.: 134,028

[22] Filed: Dec. 17, 1987

Related U.S. Application Data

[63] Continuation-in-part of Ser. No. 20,808, Mar. 2, 1987, Pat. No. 4,885,250.

[51] Int. Cl.$^5$ .................... C12N 11/06; C12N 11/08; G01N 33/549; C07K 17/08
[52] U.S. Cl. .......................................... 435/181; 435/7; 435/180; 435/803; 435/815; 435/817; 436/531; 436/532; 436/824; 530/815; 530/816
[58] Field of Search .................. 435/7, 180, 181, 182, 435/803, 815, 817; 436/528, 531, 532, 824; 530/815, 816

[56] References Cited

U.S. PATENT DOCUMENTS

| | | | |
|---|---|---|---|
| 3,843,443 | 10/1974 | Fishman | 195/63 |
| 4,119,897 | 10/1976 | Hato et al. | 435/182 |
| 4,177,038 | 12/1979 | Biebricher et al. | 435/181 X |
| 4,317,879 | 3/1982 | Busby et al. | 435/14 |
| 4,412,000 | 10/1983 | Lehmann et al. | 435/181 X |
| 4,619,904 | 10/1986 | Giaever et al. | 436/528 X |

FOREIGN PATENT DOCUMENTS

0011504 7/1983 European Pat. Off. .

OTHER PUBLICATIONS

Danielson et al., Biotechnology and Bioengineering, 23, 1919–1917 (1981).
Weetall, Methods in Enzymology, vol. XLIV: Immobilized Enzymes, Chapter 10, 134, Ed. K, Mosbach, Academic Press, New York (1976).

*Primary Examiner*—David M. Naff
*Attorney, Agent, or Firm*—George A. Frank

[57] ABSTRACT

A bioaffinity separation method is provided along with a solid affinity support utilized in that method. Additionally, immobilized enzyme systems are provided for use as enzyme electrode systems. The support is based on an inert perfluorocarbon polymer carrier with ligands or binders attached to its surface through a highly fluorinated isocyanate anchor group. Methods for preparing such supports and their use in capturing target molecules from samples and in analytical applications are also provided.

25 Claims, No Drawings

ENZYME IMMOBILIZATION AND BIOAFFINITY SEPARATIONS WITH PERFLUOROCARBON POLYMER-BASED SUPPORTS

CROSS REFERENCE TO RELATED APPLICATION

This application is a continuation-in-part of application Ser. No. 20,808, filed Mar. 2, 1987, now U.S. Pat. No. 4,885,250.

TECHNICAL FIELD

This invention is related to the performance of affinity separations and more specifically to enzyme immobilization and the performance of bioaffinity separations utilizing solid perfluorocarbon polymer-based supports and their use in capturing molecules through specific binding reactions.

BACKGROUND ART

An affinity separation can be defined as any separation achieved by employing the specific binding of one molecule by another. Bioaffinity separation is defined as an affinity separation in which one of the components involved in the affinity reaction is biologically active or is of biological interest. Bioaffinity separations generally involve at least one biomacromolecule, such as a protein or nucleic acid, as one of the components of the binding pair. Examples of such bioaffinity binding pairs include: antigen-antibody, substrate-enzyme, effector-enzyme, inhibitor-enzyme, complementary nucleic acid strands, binding protein-vitamin, binding protein-nucleic acid; reactive dye-protein, reactive dye-nucleic acid; and others; the terms ligand and binder will be used to represent the two components in specific bioaffinity binding pairs.

Affinity separations are generally considered to require the use of solid carriers derivatized with a ligand or binder. These separations can be carried out as batch processes or chromatographic processes with the latter generally being preferred. Affinity chromatography is well known and has been reviewed, for example, in C. R. Lowe, "An Introduction to Affinity Chromatography", North Holland publishing Company, Amsterdam, N.Y. 1978. Lowe describes the characteristics desirable in a solid support to be used in an affinity separation. According to Lowe, the solid support should form a loose, porous network to allow uniform and unimpaired entry and exit of large molecules and to provide a large surface area for immobilization of the ligand; it should be chemically inert and physically and chemically stable; and the support must be capable of functionalization to allow subsequent stable coupling of the ligand. Additionally, the particles should be uniform, spherical and rigid to ensure good fluid flow characteristics.

The list of support materials suitable for affinity chromatography is extensive and will not be reviewed here (see Lowe, 1978, for a partial listing). It is not generally possible for a given support to achieve all of the above objectives. One requirement faced in preparing affinity supports from any carrier is the efficient and stable attachment of the ligand or binder to the carrier. The most common method employed is covalent attachment generally by modification of the carrier surface with a reactive reagent which then covalently bonds to the ligand or binder. Representative examples of this approach are given by Weetal [Methods in Enzymology, Volume XLIV: Immobilized Enzymes, Chapter 10, 134. Ed. K. Mosbach, Academic Press, New York, (1976)]. The major disadvantages of this approach are as follows: modification of the surface properties of the carrier which frequently results in increased nonspecific binding of unwanted proteins; inactivation of a significant portion of ligands or binders being bound; and the permanence of the attachment preventing recovery of scarce or expensive ligand or binder.

Another common attachment method is the nonspecific adsorption of the ligand or binder to the carrier. This approach is reviewed by Messing [Methods in Enzymology, Volume XLIV:Immobilized Enzymes, Chapter 11, 149, Ed. K. Mosbach, Academic press, New York, (1976)]. The major disadvantages of this approach are: relatively weak attachment, some or all of the bound ligand or binder is generally released during use; and partial inactivation of the ligand or binder being attached to the carrier. Despite these disadvantages this approach is still widely used due to its inherent simplicity.

Fluorocarbon polymers have been used as carriers to which ligands have been attached by adsorption [U.S. Pat. No. 3.843 443 issued to Fishman on Oct. 22, 1974; WO 8603-840-A filed by Rijskuniv Groningen; and Siergiej, Dissertation Abstracts, Int. B., Volume 44, 153 (1983)]. No attempt was made to modify the ligands to effect a specific interaction between the ligand and the carrier. Sakagani et al. [EP No. 0,011,504, published July 20, 1983] disclose the use of electrodeposition to attach ligands to fluoropolymer ion-exchange membranes. Again, no attempt was made to modify the ligand to effect a specific interaction between the ligand and the carrier.

Busby et al. (U.S. Pat. No. 4,317,879, issued Mar. 2, 1982) disclose the covalent attachment of an enzyme, glucose oxidase, to a fluorocarbon membrane through paraformaldehyde linking.

Hato et al. (U.S. Pat. No. 4,619,897, issued Oct. 23, 1986) disclose the immobilization of enzymes onto a fluorine resin membrane which is made hydrophilic on one side by the penetration of a perfluoroalkyl surface active agent to a prescribed depth. The asymmetrically functional membrane thus obtained is then treated with an enzyme and a crosslinking agent such as glutaraldehyde to achieve enzyme immobilization. The product could be utilized as an enzyme electrode.

Copending U.S. Pat. application, Ser. No. 863,607, filed May 15, 1986, discloses perfluorocarbon fluid-based liquid supports prepared by partitioning perfluoro-substituted ligands or binders to the surface of droplets of an emulsion of liquid perfluorocarbons.

Affinity separations often form a component part of other processes. One example is their use in heterogeneous immunoassays. Here the affinity separation is used to capture an analyte from a complex mixture such as serum or plasma. After capturing the analyte, the contaminants are washed away and the analyte is detected using well known assay protocols.

Some common solid supports in this area are plastic spheres (beads), interiors of plastic test tubes, interiors of microtitre plate wells, magnetic particles, and porous glass particles. One disadvantage of these systems is the difficult and inefficient attachment of ligand or binder to the support.

Certain separation problems have been traditionally dealt with by liquid-liquid extractions. For example, in nucleic acid hybridization assays, requiring purified nucleic acid, a nucleic acid from the sample, such as DNA or RNA, needs to be bound to a solid support. To obtain the nucleic acid to be probed it must first be released from a cell (if within a cell), by lysis, then extracted from the lysate. The most common extraction technique uses an aqueous phenol/chloroform mixture (Maniatis et al., Molecular Cloning: A Laboratory Manual, pp. 458–9. Cold Spring Harbor Laboratory, 1982). Proteins, which are the major component of the lysate, tend to interfere with the extraction. Following extraction of the nucleic acid, excess phenol must be extracted with ether and then the ether evaporated. The nucleic acid containing solution is then concentrated prior to deposition on a solid support; see, for example, Church et al, proc. Nat. Acad. Sci. USA, Volume 81, 1991 (1984). This is a tedious and hazardous process with many opportunities for material losses along the way.

Because affinity separation is a powerful technique and because currently available supports suffer from various disadvantages, there is a need for improved supports. These should have the following properties: physical and chemical stability; chemical inertness; compatibility with a variety of biological samples; utility in batch and chromatographic applications; high surface area; ability to allow high flow rates in chromatographic applications; ability to provide for ready and stable attachment of ligands or binders to the surface; and allow simple efficient regeneration of the support.

DISCLOSURE OF THE INVENTION

The affinity supports of this invention are based on solid perfluorocarbon polymer carriers to which ligands or binders are securely attached through a highly fluorinated isocyanate anchor group. The affinity supports are chemically inert and have low nonspecific binding to the ligands and binders.

The method of conducting bioaffinity separations comprises the steps of:

(1) forming a solid affinity support by attaching a ligand or binder to the surface of a solid perfluorocarbon polymer carrier through a highly fluorinated isocyanate anchor group; and (2) capturing a target binder or ligand, complementary to the ligand or binder attached to the carrier from a mixture using said affinity support.

The ligand or binder is attached to the surface by modification of the ligand or binder with a highly fluorinated isocyanate anchor group to allow secure attachment to perfluorocarbon polymers. The anchor group is based on a compound having the formula $R_F$—$CH_2CH_2CH_2$—$NCO$, wherein $R_F$ is a linear, branched or carbocyclic perfluorinated radical containing 1–20 carbon atoms.

DISCUSSION OF THE INVENTION

The perfluorocarbon polymer-based solid affinity supports of this invention offer unprecedented advantages in carrying out bioaffinity separations. The greatest advantages of using solid perfluorocarbon polymer-based affinity supports relate to the inertness and rigidity of the carrier. Other advantages are allowing recovery of scarce or expensive ligand o binder and the attachment of ligands or binders with known activity. The solid perfluorocarbon polymer-based supports of this invention offer additional advantages such as being stable in an aqueous environment and being amenable to treatment to achieve low nonspecific binding to native proteins. nucleic acids or other components of biological samples.

The supports of this invention comprise solid perfluorocarbon polymer carriers and securely attached ligands or binders. By perfluorocarbon is meant a molecule which contains the largest possible or a relatively large proportion of fluorine atoms in its structure. Perfluorocarbon polymers are known to be inert. Some perfluorocarbon polymers which can be used to form the solid affinity supports of this invention are: various Teflon ® fluorocarbon polymers, polytetrafluoroethylene, polyvinylfluoride, and polyvinylidene difluoride. (Teflon ® is a registered trademark of E. I. du Pont de Nemours and Company.)

By ligand is meant an antigen, hapten, nucleic acid, enzyme substrate, vitamin, dye or other small organic molecule including enzyme substrates, effectors and inhibitors and by binder is meant an antibody, enzyme, nucleic acid, binding protein, synthetic mimics of binding proteins such as polylysine and polyethyleneimines or other biomacromolecule capable of specific binding, enzyme/substrate, etc. interactions.

The highly fluorinated isocyanate anchor group is based on a compound having the formula $R_FCH_2CH_2CH_2NCO$, wherein $R_F$ is a linear, branched or carbocyclic perfluorinated radical containing 1–20 carbon atoms. In a preferred class of the above compounds, $R_F$ is a linear $F(CF_2)_n$ radical. A more specifically preferred compound is $F(CF_2)_8CH_2CH_2CH_2NCO$. These compounds are described in applicants' assignee's copending application Ser. No. 07/134,027, filed on even date herewith, now abandoned, incorporated herein by reference.

The affinity support must have the ligand or binder securely attached to the carrier. By secure attachment is meant an attachment capable of surviving the steps involved in the use of the solid supports of this invention such as in bioaffinity separations. However, it is expected that this attachment needs to be reversible when desired, for example, when desiring to regenerate the carrier, such as by displacement of ligand or binder by chaotropic agents. Secure attachment is necessary so that ligand or binder does not contaminate the purified product and also to prevent loss of capacity of the support. With prior supports this is usually accomplished by covalently attaching the ligand or binder to the support. In addition to attaching ligand or binder securely, it is desirable not to alter the general inertness of the carrier nor to introduce functional groups which might increase nonspecific binding. Further, it is desirable to develop general methods which can be applicable to a variety of ligands or binders.

The preferred method for preparing perfluorocarbon polymer-based affinity supports is referred to as the partition or adsorption method. In this method the ligand or binder is modified to permit its selective high affinity (secure) binding to the surface of the perfluorocarbon carrier. One means to accomplish this is to prepare and purify a perfluorocarbon-substituted ligand or binder prior to attachment to the surface. For convenience, the perfluorocarbon groups attached to a ligand or binder are called anchor groups. Several well known chemical strategies can be used to attach covalently highly fluorinated groups to ligands or binders. Factors which should be considered are reactivity of the fluorinated compound used, the pH of the reaction medium, and the time and temperature of the reaction.

Compounds such as the acid chlorides, anhydrides and imidazolides of various perfluorocarbon acids, for example, perfluorooctanoyl chloride, perfluorooctyl acetyl and propanoyl chlorides and perfluorooctanoyl and perfluorooctyl propanoyl imidazolides have been used successfully during the preparation of the solid supports of this invention. Of these, the imidazolide derivative is preferred due to its lower reactivity allowing more controllable reactions. The most preferred class of compounds is the highlY fluorinated isocyanates as described above, an example being perfluorooctylpropyl isocyanate. The isocyanates are most preferred because of their increased stability to hydrolysis at the slightly alkaline reaction conditions generally used during the preparation of the fluorocarbon-substituted ligand or binder. In addition, the small amount of hydrolysis products formed (amines and ureas) do not interfere with the adsorption of the modified ligand or binder to the surface of the perfluorocarbon polymer-based solid support. This eliminates the need to purify the modified ligand or binder from the reaction milieu in which it was prepared prior to forming the perfluorocarbon polymer-based solid support of this invention.

In general, the modification reactions are carried out by mixing an aqueous solution of the ligand or binder with the fluorinated isocyanate reagent dissolved in a water miscible organic solvent such as tetrahydrofuran under controlled time, temperature and pH conditions. The derivatized ligand or binder can be separated from the by-products of the reaction and the organic solvent by gel filtration or dialYsis. The degree of derivatization can be determined by any of the known techniques such as trinitrobenzene sulfonate labeling. The substituted ligand or binder is now ready to be used to form the perfluorocarbon polymer-based solid support with an appropriate carrier.

The affinity support can be formed by mixing a perfluorocarbon polymer carrier such as Teflon ® P PFA powder coating with a buffered solution of the derivatized ligand or binder which partitions onto the surface of the carrier. It is advantageous that the carrier be treated with an organic solvent such as methanol or t-butanol prior to contacting with the buffered solution. The solvent treatment can improve the wettability of the carrier and can result in faster and better immobilization. Batch processes generally gave higher levels of attachment than chromatographic processes.

The degree of derivatization (substitution) required to provide secure attachment to the surface of the carrier is expected to vary significantly depending upon the nature of the highly fluorinated anchor group, the spatial arrangement of the anchor groups on the ligand, the size and nature of the ligand, and the eventual use of the support. In general, the higher the degree of substitution the stronger the attachment. This, however, can be limited by, steric considerations as well as the need to retain the biological activity of the ligand or binder. It has been found that placing anchor groups on approximately 20% of the available amino groups on a typical protein is preferred. When 20% of the amino groups of horseradish peroxidase and urease were labeled with perfluorooctylpropanoyl imidazolide, the enzyme was found to lose only 12% of its native activity. Also, when washed with buffers, the enzymes resisted being washed off the surface of the carrier.

While the approach described above provides a good general procedure for attaching ligands or binders to the surface of the carriers, specific procedures for specific ligands or binders may need to be utilized. One such procedure would involve specific substitution of the Fc portion of an IgG class antibody with a highly fluorinated reagent allowing the attachment of the antibody to the perfluorocarbon carrier in a specific orientation. This would allow attachment of the antibody with its specific binding portions, the F(ab) binding sites, oriented into the aqueous environment. Such orientation is expected to provide more efficient use of the antibody and greater capture efficiency. It might also minimize nonspecific binding interferences by rheumatoid factors which might be present in the mixture by making the Fc portion of the antibody inaccessible to the aqueous phase.

The method of preparation described above provides many advantages. These include providing for preparation of individual components of the solid affinity support permitting more rigorous quality control; promoting optimal use of expensive or scarce ligands or binders; creating a single ligand layer minimizing steric blockage of binding sites on the support; and providing multiple attachment sites on each ligand or binder promoting stronger attachment to the surface of the carrier.

Another advantage of the solid perfluorocarbon polymer-based supports of this invention over conventional supports is the ability to sterilize the reagents used to form the support as well as to re-sterilize contaminated supports. The latter is not possible with conventional supports. The partition method of attaching ligands or binders to the carrier is particularly, amenable to re-sterilization. The perfluoro-derivatized ligand or binder can be recovered from the support using chaotropic agents and sterilized by ultrafiltration prior to reattachment. Chaotropic agents which have been found effective in removing ligands from perfluorocarbon affinity supports are high concentrations of fluorosurfactants. Various water miscible organic solvents such as methanol are also effective in removing ligands.

While perfluorocarbons are inert and display relatively low nonspecific binding characteristics, some nonspecific binding does occur (see for instance Fishman supra). The nonspecific binding of these carriers can be further decreased by treatment with low concentrations of nonionic fluorosurfactants such as Zonyl ® FSN fluorosurfactant, a perfluoro-polyoxyethylene surfactant. The fluorosurfactant appears to coat the surface of the carrier preventing binding of other materials. These fluorosurfactants can also prevent the binding of the modified ligands or binders and, therefore, this treatment must be carried out after the formation of the affinity support. The fluorosurfactants will not, however, cause the release of the specifically modified ligands or binders from the carrier.

The perfluorocarbon-polymer based supports can also be sterilized by autoclaving. The support can then be reformed using the same components or fresh polymer could be substituted. This allows recovery and reuse of valuable ligand or binder. Certain supports can also be sterilized without separation of the components if the ligand or binder can retain biological activity under appropriate sterilization conditions. These considerations are particularly important to applications such as extracorporeal blood processing or preparation of therapeutics for use in humans.

The use of solid perfluorocarbon polymer-based affinity supports in extracorporeal blood depletion therapy also offers another unique advantage. An uncoated and unmodified perfluorocarbon column or filter can be placed downstream from the depletion column so that if any trace amounts of perfluorinated ligand or binder is released from the depletion column, it will be bound by the uncoated perfluorocarbon.

Another application of the solid affinity supports of this invention is their use to capture DNA from solution. A perfluorocarbon polymer-based affinity support was prepared through the partition method with histone proteins attached to the surface of the support. Histones are highly positively charged proteins which interact with DNA in the cell to package the DNA into a compact form. Surprisingly, it has been found that a perfluorocarbon polymer-based affinity support prepared from modified calf thymus histones and porous PTFE membranes or other carriers can capture DNA. from aqueous solution. While histones were used in the described process, other ligands such as polylysine, anti-DNA antibodies and specific oligonucleotide sequences capable of capturing only complementary base sequences, can also be utilized.

Another application which illustrates the advantages of the use of perfluorocarbon polymer-based affinity supports, is the immunoassay. One such assay is a qualitative enzyme linked immunosorbent assay (ELISA) in which color can be visually detected on the surface of filter paper, porous membrane, plastic paddle or other solid surfaces. This assay can be readily adapted to quantitative assays and to the use of other detectable signals besides color. It is anticipated that a particularly advantageous application of the affinity supports of this invention would be achieved if only portions of a carrier were highly fluorinated so that the ligand or binder could be attached only to discrete portions of the carriers. This might be achieved by coating portions of a hydrocarbon polymer with Riston ® photopolymer resist material, exposing to light areas where no binding of ligand to carrier is desired, dissolving unexposed resist material, and then exposing the bare hydrocarbon regions to fluorine gas. The highly fluorinated portions could then function as described to bind modified ligand or binder.

Yet another application is in the construction and use of immobilized enzyme systems such as enzyme electrodes by immobilizing enzymes onto solid perfluorocarbon polymer-based supports. In this application, an enzyme can be bound to a fluorocarbon membrane of an electrochemical gas-sensor (e.g., $O_2$ and $NH_3$). The enzyme is chosen to be able to catalyze a reaction which generates a product or consumes a coreactant which can be monitored electrochemically. The electrochemical signal provides a measure of the analyte concentration. In this application, the enzyme acts as the binder and the target analyte as the ligand.

A urea sensitive electrode can be constructed by binding the enzyme urease to a Teflon ® perfluorocarbon membrane of an ammonia gas-sensor. The urease can be bound to the Teflon ® perfluorocarbon membrane using the partition method. It is advantageous to use a microporous membrane in order to increase the amount of urease bound. In addition to the advantages noted above, this application also benefits from not having to employ a second support membrane frequently required for binding of the enzyme.

The following examples further illustrate the invention.

EXAMPLE 1

Demonstration of Adsorption of a Perfluoroalkyl Substituted Protein to Solid Fluorocarbon Surfaces (Perfluorooctyl)propanoyl imidazolide. 1H,1H,2H,2H-perfluoroundecanoic imidazolide, was prepared from perfluorooctylpropionic acid as follows: 4.9 g of perfluorooctylpropionic acid (ICN Biomedicals, Inc., Plainview, N.Y.) was dissolved in 15 mL of dry tetrahydrofuran and added to a stirred solution of 1.8 g of 1,1'-carbonyldiimidazole (Sigma Chemical Co., St. Louis, Mo.) in 35 mL of dry THF at room temperature. The reaction mixture was stirred for 30 minutes, during which time the product began to crystallize. The mixture was cooled in ice-water and filtered in a glass-fritted filter funnel. The crystals were washed with ice-cold, dry THF and dried with a stream of dry air. The yield of(perfluorooctyl)propanoyl imidazolide was 3.8 g, 68% of the theoretical yield. The melting point of the product was 128° C.

Fluorescently labeled human gamma-globulin (FITC-hIgG) was prepared by adding 1.0 mg of fluorescein isothiocyanate (FITC) suspended in 2 mL of 0.1M disodium hydrogen phosphate solution to 80 mg of human gamma-globulin (Sigma Chemical Co., St. Louis, Mo.) dissolved in 5.0 mL of 0.2M disodium hydrogen phosphate solution. The pH of the stirred mixture was adjusted to 9.5 by the addition of 0.1M trisodium phosphate solution and the total volume increased to 8.0 mL by the addition of 0.145M sodium chloride solution. The reaction mixture was stirred for 30 minutes at room temperature. The reaction mixture was applied to a 25×2.2 cm column of Bio-Gel ® P6 (Bio-Rad laboratories, Richmond, Calif.) equilibrated with phosphate buffered saline. The FITC-hIgG was eluted in the exclusion volume of the column, free of unreacted and hydrolized FITC. Spectrographic analysis of the FITC-hIgG showed that the degree of conjugation was 3.34 moles of FITC per mole of gamma-globulin.

To 6.75 mg of the FITC-hIgG, prepared as above. dissolved in ice-cooled 0.1M phosphate buffer, pH 8.0, was added 0.5 mL of a THF solution of (perfluorooctyl)propanoyl imidazolide containing 20 mg per mL. he reaction mixture was stirred in an ice bath for two hours. The reaction mixture was applied to a 3×26 cm column of Bio-Gel P6, equilibrated with phosphate buffer, pH 8.0. The perfluoroalkylated protein was eluted in the void volume of the column and was collected in about 21 mL. The degree of reaction was determined as follows: An aliquot of the eluted protein fraction was analyzed for remaining amino groups by standard procedures using trinitrobenzene sulfonic acid. The amount of substitution of the hIgG was calculated from the difference in the amount of available amino groups present between a control (no imidazolide treatment) and the preparation. The percentage of the available amino groups reacted was 30%.

The following materials were immersed in 0.5 mL aliquots of the perfluoroalkylated FITC-hIgG solution and mixed for about 15 secs:

a. PTFE (polytetrafluoroethylene) membrane (8.2 mm dia., 1 micron pores, #TE37, from Schleicher & Schuell Inc., Keene. N.H.)

b. Ammonia porous PTFE membrane, #95-10-04 (Orion Research Inc., Cambridge, Mass.)

c. 5.0 mg sample of Nensorb, 325 mesh (E. I. du Pont de Nemours, and Company, Wilmington, Del.).

After treatment the materials were washed three times in 3 mL aliquots of phosphate buffer, pH 8, and examined under a fluorescence microscope. All samples showed a brilliant fluorescence, demonstrating strong adsorption of the perfluoroalkylated FITC-hIgG to the fluorocarbon surfaces. Treatment of the samples with a 0.1% solution of a fluorosurfactant (Zonyl® FSC) failed to desorb the fluorescent protein.

EXAMPLE 2

Preparation of an Immobilized Enzyme on a Fluorocarbon Matrix

Horseradish peroxidase (Donor:hydrogen-peroxide oxidoreductase; EC 1.11.1.7) was perfluoroalkylated by the method described in Example 1. 10 mg of horseradish peroxidase (HRP), obtained from Sigma Chemical Co., St. Louis, Mo., was treated with 20 mg (perfluorooctyl)propanoyl imidazolide in THF and purified on a Bio-Gel P6 column as previously described. The product showed a relative activity of 0.36 mg per mL, compared to untreated enzyme, as measured by the standard method using tetramethylbenzidine as a chromogenic substrate.

A small glass column was dry-packed with 1.04 g of Nensorb (E. I. du Pont de Nemours and Company, Wilmington, Del.) and percolated with methanol methanol/water; 1:1 and a buffer prepared from 48.6 mL of 0.1M citric acid plus 51.4 mL of 0.2M disodium hydrogen phosphate (C/P buffer). Aliquots of various dilutions of the perfluoroalkylated HRP (PF-HRP) in C/P buffer were added to this column and the eluants assayed for HRP activity using the standard method. A total of 970 μg of PF-HRP was found by difference to have adsorbed to the Nensorb. After adsorption, the column was washed ten times with 10 mL aliquots of C/P buffer. Assay of the first seven washings revealed a total of 154 ng (0.016% of amount bound) of peroxidase activity had been displaced from the column; the final three washes indicated no peroxidase activity. The minimal detectable limit of the standard HRP assay is equivalent to approximately 0.1 ng per mL.

The column was now washed with 10 mL aliquots of C/P buffer containing 1% Zonyl FSC fluorosurfactant (E. I. du Pont de Nemours and Company) and the eluants assayed for enzymic activity. The first aliquot contained a total of 212 ng HRP activity; the second 27 ng and the third 7 ng. Thereafter, the column eluants contained no measurable peroxidase activity thus demonstrating the very strong adsorption of the PF-HRP to the fluorocarbon matrix even in the presence of fluorosurfactant. Finally, the presence of immobilized peroxidase on the support was vividly demonstrated by application of peroxide and chromogenic substrate when a dark blue color rapidly developed.

EXAMPLE 3

Preparation of a DNA Extraction Membrane

Perfluoroalkylated calf thymus histones were prepared using a slight modification of the method described in Example 1. To 10 mL of a 1 mg per mL solution of calf thymus histone (Sigma Chemical Co., St. Louis, Mo.) in phosphate buffer, pH 8, was added 4 mg of (Perfluorooctyl)propanoyl imidazolide dissolved in 0.2 mL of dry THF. After stirring in an ice bath for two hours, the reaction mixture was purified on a Bio-Gel® P6 column as previously described. Analysis for degree of available amino group substitution showed about 92% reaction.

A PTFE porous membrane (Type TF 450. Gelman Sciences Inc., Ann Arbor, Mich.) was immersed in the solution of purified perfluoroalkylated histone and washed three times in phosphate buffer. The membrane was then immersed in a solution of 10 μg/mL of Strain B E. coli DNA (Sigma Chemical Co., St. Louis. Mo.) in phosphate buffer and gently rocked for three hours. The membrane was removed, washed three times in buffer and immersed in a 10 μg/mL solution of acridine orange to stain any adsorbed DNA. The membrane was then washed in a stream of distilled water and observed under a fluorescence microscope. The treated membrane was visibly fluorescent indicating the presence of adsorbed DNA. An untreated membrane reacted with the acridine orange solution showed no visible fluorescence.

A markedly improved adsorption of the DNA, as demonstrated by, a relatively higher intensity of fluorescence, was obtained by pretreatment of the membrane with a 0.1M phosphate buffer. pH 8, containing 10% tert.butanol and 2% Tween 20, before adsorption of the perfluoro-alkylated histone.

EXAMPLE 4

Preparation and Use of an Immunoaffinity Fluorocarbon Support

Perfluoroalkylated human immunoglobulin (PF-hIgG) was prepared as described in Example 1. It was purified on a Bio-Gel® P6 column and collected in 0.1 M phosphate buffer, pH 8. From the results of previous experiments, performed under identical conditions, the degree of perfluoroalkylation is assumed to be about 20% of the available amino groups.

10 mL of a 304 μg/mL buffered solution of PF-hIgG was rotationally mixed overnight with 2.1 g of Teflon powder (E. I. Du pont de Nemours and Company, Wilmington Del.). The total amount of PF-hIgG adsorbed was determined spectroscopically by difference and found to be 2.64 mg. The antigen support was transferred quantitatively to a small chromatographic column attached to a pharmacia FPLC chromatography system with peak integration facilities provided by a Spectra-physics SP4100 computing integrator. The column was thoroughly washed with a 0.2% aqueous solution of Zonyl® FSN (E. I. du Pont de Nemours and Company) reduce nonspecific binding to fluorocarbon based support matrices.

To assess the amount of binding of nonspecific immunoglobulin by the column, 0.5 mL samples of a 421 μg/mL solution of goat IgG in 0.1M sodium citrate buffer, pH 8, containing 0.0085M sodium chloride and 0 2% Zonyl FSN, were injected onto the column. The recovery of the eluted goat IgG was found to be 100%, by comparison with peak area values obtained by direct passage through the detection system (no column present) of equivalent protein samples. The adsorption of nonspecific immunoglobulin can therefore be considered negligible.

A series of affinity separations for the purification of goat anti-human IgG immunoglobulin was performed by repetition of the following cycle:

1. Injection of 0.5 mL of a 400 μg/mL solution of goat anti-human IgG immunoglobulin (Jackson ImmunoResearch Labs, Avondale, Penna.) in 0.1M sodium citrate, pH 8, containing 0.0085M sodium chloride and 0.2% Zonyl FSN.

2. Washing the column with 0.1M sodium citrate, pH 8, containing 0.0085M sodium chloride and 0.2% Zonyl FSN, until base line on the adsorbance recorder is reached (about five column volumes). The integrated value of the resulting peak represents the 'unadsorbed' fraction of the applied sample.

3. Washing the column with 0.1M sodium citrate, pH 3, until base line returns to zero. The integrated value of the resulting peak represents the 'desorbed' specific antibody from the applied sample.

4 Washing the column with about ten column volumes of the pH 8 citrate buffer.

This cycle was repeated 41 times resulting in the following observations. The integrated peak value of the 'unadsorbed' fraction of the sample had a mean value of 91.7+3 $\mu$g for the first nine applications. Thereafter up to cycle 25 the value increased steadily up to a recovery of 120 $\mu$g. It was felt that this phenomena was due to gradual deterioration of the antibody sample caused by continued storage at room temperature. This was confirmed by replacement with a freshly prepared antibody solution when the values obtained over the remainder of the experiment returned to a mean of 96+10 $\mu$g per application. Except for the first cycle, the integrated peak areas of the 'desorbed' specific antibody fell very gradually over the period of the experiment from about 30 $\mu$g to about 20 $\mu$g equivalents. These recoveries compare very favorably with results obtained using established affinity supports where gradual fouling of the column or an accumulation of non-dissociatable, high avidity, antibodies similarly can result in gradual loss of recovery. The experiment, however, conclusively demonstrates the utility of the fluorocarbon based affinity support for preparative purposes.

EXAMPLE 5

Urea Electrode

Perfluoro-substituted urease was prepared by adding 2 mL of perfluorooctyl propanoyl imidazolide (20 mg/mL in tetrahydrofuran) to 20 mL of urease (E.C. 3.5.1.5) solution . which contained 1 mg of type VII urease from Sigma Chemical Company St. Louis, Mo., per mL of pH 8.0 phosphate buffer. The reaction mixture was stirred for two hours in an ice bath, and then applied to a 25×2.2 cm column of Bio-Gel ® P-6 (Bio-Rad Laboratories. Richmond, Calif.), equilibrated with pH 8.0 phosphate buffer. The perfluoro-substituted urease was eluted in the exclusion volume of the column, free from unreacted imidazolide reagent. The perfluoro-substituted enzyme solution was concentrated four-fold using an Amicon 8050 Concentration system with a 100,000 molecular weight cut-off membrane (Amicon Corporation, Lexington, Mass.).

The urea enzyme electrode was prepared by first wetting the microporous Teflon membrane of an ammonia gas-sensing electrode (Orion Model 92-10, Orion Research Inc., Cambridge. Mass.) by dipping it into an aqueous solution containing 10% t-butanol and 2% Tween by volume. The excess wetting solution was blotted off and the membrane was placed into the concentrated perfluoro-substituted urease solution for 5 minutes. The membrane was dried under vacuum in a dessicator, after which the exposure to the enzyme solution was repeated. After drying again in the dessicator, the membrane was placed into the body of the ammonia electrode and the electrode was assembled as recommended by the manufacturer.

The response of the urea electrode was tested by placing it into 25.00 mL of pH 8.5 Tris buffer, containing 1×10E-3 M EDTA, and making additions of a stock solution of 0.1M urea, prepared in the Tris buffer. The steady-state potential readings were measured after each addition with a Model 130 pH/mV meter (Corning Science products, Medfield, Mass.); typical response is shown in Table 1. For comparison, the response obtained with a urea electrode prepared using unmodified urease is also included.

TABLE 1

| Urea Concentration (M) | Potential Perfluoro-substituted Urease Electrode (mV) | Potential Unmodified Urease Electrode (mV) |
| --- | --- | --- |
| 0 | 173.7 | 186.7 |
| 4.00 × 10E-5 | 143.6 | 185.0 |
| 1.20 × 10E-4 | 121.0 | 182.1 |
| 3.19 × 10E-4 | 100.1 | 177.2 |
| 7.15 × 10E-4 | 80.8 | 167.0 |
| 1.50 × 10E-3 | 64.7 | 158.4 |

The response slope of urea electrodes prepared with perfluoro-substituted urease of this invention was typically between 45 to 50 mV/decade. This response remained stable for at least five days when the electrode was stored in buffer at room temperature. The electrode prepared using the same procedure with unmodified urease gave very little response, i.e., response slope of 16.8 mV/decade, indicating that perfluoro-substitution of the enzyme is required for maximum adsorption.

The time required for the urea electrode to reach a steady-state potential was 4 minutes for a concentration change from 1×10E-5 to 1.0×10E-4M urea, and 3 minutes for a change from 1.0×10E-4 to 1.0×10E-3M urea. No leaching of the perfluoro-substituted urease enzyme from the membrane was detectable in the buffer solution after four days of soaking.

EXAMPLE 6

Capture of IgG

A modified Protein A was perfluoroalkylated by dissolving 100 mg of a recombinant modified Protein A (expressed in E. Coli and lacking C-terminal domain, obtained from portion products Ltd., U.K.) in 100 mL of 0.10M phosphate buffer, pH 8.5 (PB). Next, 19.6 mL of a 0.05% (v/v) solution of perfluorooctylpropyl isocyanate in dioxane was added to 98.0 mL of the modified Protein A solution. The reaction mixture was mixed gently and allowed to react for 7 hours at room temperature and then overnight at 4° C. The reaction mixture was then centrifuged at 3,000 rpm for 5 min. to remove any denatured protein or other insoluble reaction by-products.

The degree of substitution on the modified Protein A by the isocyanate was determined by determining the remaining available amino groups by standard procedures using trinitrobenzene sulfonic acid. The amount of substitution was calculated from the difference in the amount of available amino groups between a control (no isocyanate treatment) and the isocyanate-treated modified Protein A. The average number of amino groups reacted on the modified Protein A molecule was found to be 3.

A solid affinity support was prepared by filling a column with 3.2 g of a heat-treated polytetrafluoroethylene resin with a nominal particle size of 35 microns (available from E. I. du Pont de Nemours and Company. Wilmington, Del. 19898). The resin was activated by pumping 20 mL of methanol (flow rate of 2 mL/min.), followed by 20 mL of a 50% (v/v) solution of methanol in water, followed by 20 mL of 0.10M sodium phosphate 0.02% (w/v) $NaN_3$, pH 8.5 buffer. Next, 25 mL of a 1:1 dilution of the perfluoroalkylated modified Protein A, prepared above, with PB was pumped through the resin. The solid support so obtained was then washed with 100 mL of 0.10 M sodium phosphate, 0.02% (w/v) $NaN_3$, 0.04% (w/v) blocking agent. pH 8.5 buffer. This was followed by a 20-mL wash with 0.01M sodium phosphate, 0.02% (w/v) $NaN_3$, pH 8.5 buffer. The blocking agent was prepared by first preparing $F(CF_2)_6CH_2CH_2OH$. This alcohol, in turn, was prepared by reacting $F(CF_2)_6CH_2CH_2I$ with sulfuric acid followed by hydrolysis to give the alcohol. The iodide was obtained by distillation of Zonyl ® TelB fluorochemical intermediate (a registered trademark of E. I. du Pont de Nemours and Company). The blocking agent was prepared by reacting the alcohol (prepared above) with ethylene oxide in the presence of a mixed catalyst ($NaBH_4$ and NaH) at 110° C. The ethylene oxide was bubbled through the reaction mixture until the equivalent of an average of 12 units of ethylene oxide had been added to the alcohol. The reaction mixture was then neutralized with acetic acid. The blocking agent so produced has the average structure:

$$F(CF_2)_6(CH_2)_2-O-(CH_2CH_2O)_{12}H$$

The binding capacity of this support for IgG was determined by passing 2.6 mL of a 5 mg/mL solution of human IgG over the support to saturate all available binding sites. After washing, bound IgG was eluted and the binding capacity of the column was determined to be 7 mg of IgG. This indicates that the modified protein A attached to the surface of the carrier remained active and that there was, in fact, secure attachment of a binder to the solid perfluorocarbon polymer carrier.

We claim:

1. A solid support containing an attached ligand or binder for the ligand consisting essentially of:
   (A) a chemically inert, water immiscible solid perfluorocarbon polymer carrier having low nonspecific binding to a ligand or binder for the ligand;
   (B) a highly fluorinated isocyanate-modified ligand or binder for the ligand securely but reversibly attached to the surface of said carrier through said highly fluorinated isocyanate; and
   (C) a nonionic fluorosurfactant coating on said carrier.

2. The support of claim 1, wherein said ligand is selected from the group consisting of nucleic acid, and dye.

3. The support of claim 1, wherein said binder for the ligand is selected from the group consisting of antibody, enzyme and nucleic acid.

4. The solid support of claim 1 wherein the highly fluorinated isocyanate is a compound of the formula $$R_F-CH_2CH_2CH_2NCO$$

wherein $R_F$ is a linear, branched or carbocyclic perfluorinated radical containing 1–20 carbon atoms.

5. The solid support of claim 4 wherein $R_F$ is $F(CF_2)_8$.

6. The support of claim 1, wherein the carrier is selected from the group consisting of polytetrafluoroethylene, polyvinylfluoride and polyvinylidene difluoride.

7. The support of claim 1, wherein said ligand is a hapten.

8. The support of claim 1, wherein said ligand is an antigen.

9. The support of claim 1, wherein said ligand is selected from the group consisting of enzyme substrates, effectors and inhibitors.

10. The support of claim 1, wherein said binder for the ligand is a binding protein or a synthetic mimic of a binding protein.

11. A bioaffinity separation process comprising the steps of:
   (A) forming a solid affinity support by
      (a) attaching a highly fluorinated isocyanate-modified ligand or binder for the ligand to the surface of a solid perfluorocarbon carrier through said highly fluorinated isocyanate and
      (b) contacting the product of step (a) with a nonionic fluorosurfactant to form an affinity support; and
   (B) capturing a binder or ligand, complementary to the ligand or binder attached to the carrier from a mixture using said solid affinity support.

12. The process of claim 11, wherein said ligand is selected from the group consisting of nucleic acid, and dye.

13. The process of claim 11, wherein said binder for the ligand is selected from the group consisting of antibody, enzyme and nucleic acid.

14. The process of claim 11, wherein said ligand is a hapten.

15. The process of claim 11, wherein said ligand is an antigen.

16. The process of claim 11, wherein said ligand is selected from the group consisting of enzyme substrates, effectors and inhibitors.

17. The process of claim 11, wherein said binder for the ligand is a binding protein or a synthetic mimic of a binding protein.

18. An immobilized enzyme system consisting essentially of:
   (A) a chemically inert, water immiscible solid perfluorocarbon polymer carrier having low nonspecific binding to a ligand or binder for the ligand;
   (B) a highly fluorinated isocyanate-modified enzyme attached securely but reversibly to the surface of said carrier through said highly fluorinated isocyanate; and
   (C) a nonionic fluorosurfactant coating on said carrier.

19. A process of preparing a solid support containing an attached ligand or binder for the ligand comprising the steps of:
   (A) modifying a ligand or binder for the ligand by attaching a highly fluorinated isocyanate anchor group to said ligand or binder for the ligand;
   (B) contacting a solid perfluorocarbon polymer with the highly fluorinated isocyanate-modified ligand or binder for the ligand to attach the ligand or binder to the polymer through said highly fluorinated isocyanate, and
   (C) contacting the product formed the step (B) with a nonionic fluorosurfactant.

20. The process of claim 19, wherein the ligand is selected from the group consisting of nucleic acid, and dye.

21. The process of claim 19, wherein said binder for the ligand is selected from the group consisting of antibody, enzyme and nucleic acid.

22. The process of claim 19, wherein said ligand is a hapten.

23. The process of claim 19, wherein said ligand is an antigen.

24. The process of claim 19, wherein said ligand is selected from the group consisting of enzyme substrates, effectors and inhibitors.

25. The process of claim 19, wherein said binder for the ligand is a binding protein or a synthetic mimic of a binding protein.

* * * * *